(12) United States Patent
Wain et al.

(10) Patent No.: US 8,997,490 B2
(45) Date of Patent: Apr. 7, 2015

(54) HEAT UTILIZATION IN ORC SYSTEMS

(71) Applicant: ElectraTherm, Inc., Reno, NV (US)

(72) Inventors: Hans Wain, Truckee, CA (US); David Williams, Carson City, NV (US)

(73) Assignee: ElectraTherm, Inc., Reno, NV (US)

( * ) Notice: Subject to any disclaimer, the term of this patent is extended or adjusted under 35 U.S.C. 154(b) by 0 days.

(21) Appl. No.: 13/758,941

(22) Filed: Feb. 4, 2013

(65) Prior Publication Data

US 2013/0199185 A1    Aug. 8, 2013

Related U.S. Application Data

(60) Provisional application No. 61/594,168, filed on Feb. 2, 2012.

(51) Int. Cl.
*F01K 25/08* (2006.01)
*F01K 23/04* (2006.01)
*F01K 23/06* (2006.01)

(52) U.S. Cl.
CPC .............. *F01K 25/08* (2013.01); *F01K 23/04* (2013.01); *F01K 23/064* (2013.01); *Y02E 20/14* (2013.01); *Y02T 10/166* (2013.01)

(58) Field of Classification Search
USPC ............................. 60/616, 618, 620, 645–681
See application file for complete search history.

(56) References Cited

U.S. PATENT DOCUMENTS

| | | | |
|---|---|---|---|
| 4,750,454 A * | 6/1988 | Santina et al. | 123/3 |
| 5,713,312 A * | 2/1998 | Waryasz | 122/481 |
| 6,510,695 B1 | 1/2003 | Fisher | |
| 6,981,377 B2 | 1/2006 | Vaynberg | |
| 2004/0020206 A1 | 2/2004 | Sullivan | |
| 2008/0168772 A1 | 7/2008 | Radcliff | |
| 2009/0188253 A1 * | 7/2009 | Smith et al. | 60/657 |
| 2009/0209025 A1 * | 8/2009 | Goschl et al. | 435/262.5 |
| 2009/0226308 A1 | 9/2009 | Vandor | |

(Continued)

FOREIGN PATENT DOCUMENTS

| | | |
|---|---|---|
| JP | 2005-000791 | 1/2005 |
| JP | 2006-037760 | 2/2006 |
| WO | WO2007033433 A1 | 3/2007 |

OTHER PUBLICATIONS

International Search Report and Written Opinion of the International Searching Authority for International Application PCT/US2013/024670, mailed May 16, 2013.

*Primary Examiner* — Thomas Denion
*Assistant Examiner* — Wesley Harris
(74) *Attorney, Agent, or Firm* — D.C. Williams

(57) ABSTRACT

Apparatus, systems and methods are provided for the improved use of waste heat recovery systems which utilize the organic Rankine cycle (ORC) to generate mechanical and/or electric power from waste heat of large industrial machines (prime movers) generating power from biofuel such as biogas produced during the anaerobic digestion process. Waste heat energy obtained from prime mover(s) is provided to one or more ORC system(s) which are operatively coupled to separate electrical generator(s). The ORC system includes a heat coupling subsystem which provides the requisite condensation of ORC working fluid by transferring heat from ORC working fluid to another process or system, such as anaerobic digester tank(s), to provide heat energy that enhances the production of fuel for the prime mover(s) without requiring the consumption of additional energy for that purpose.

55 Claims, 8 Drawing Sheets

(56) References Cited

U.S. PATENT DOCUMENTS

| | | |
|---|---|---|
| 2010/0093046 A1 | 4/2010 | Remmereit |
| 2010/0242476 A1 | 9/2010 | Ast et al. |
| 2010/0263380 A1 | 10/2010 | Biederman |
| 2011/0265698 A1* | 11/2011 | Hirson et al. ............ 110/345 |
| 2012/0111009 A1* | 5/2012 | Corry et al. ............ 60/662 |

* cited by examiner

HEAT UTILIZATION IN ORC SYSTEMS

RELATED APPLICATIONS

This application claims priority from the applicants' prior U.S. Provisional Patent Application entitled Improved Heat Utilization in ORC Systems, Ser. No. 61/594,168, filed Feb. 2, 2012, which Application is hereby incorporated by reference. In this regard, in the event of inconsistency between anything stated in this specification and anything incorporated by reference in this specification, this specification shall govern.

FIELD OF INVENTION

The present invention relates to the apparatus, systems, and methods of utilizing organic Rankine cycle systems for the generation of power from waste heat sources.

BACKGROUND

Many physical processes are inherently exothermic, meaning that some energy previously present in another form is converted to heat by the process. While the creation of heat energy may be the desired outcome of such a process, as with a boiler installed to provide radiant heat to a building using a network of conduits which circulate hot water to radiators or a furnace used for the smelting of metals, in many other instances unwanted heat is produced as a byproduct of the primary process. One such example is that of the internal combustion engine of an automobile where the primary function is to provide motive force but where the generation of significant unwanted heat is unavoidable. Even in those processes where the generation of heat energy is desired, some degree of residual heat unavoidably escapes or remains which can be managed and/or dissipated. Whether generated intentionally or incidentally, this residual, or waste, heat represents that portion of the input energy which was not successfully applied to the primary function of the process in question. This wasted enemy detracts from the performance, efficiency, and cost effectiveness of the system.

With respect to the internal combustion engine common to most automobiles, considerable waste heat energy is generated by the combustion of fuel and the friction of moving parts within the engine. Automobiles are equipped with extensive systems that transfer the heat energy away from the source locations and distribute that enemy throughout a closed-loop recirculating system, which usually employs a water-based coolant medium flowing under pressure through jackets within the engine coupled to a radiator across which the imposition of forced air dissipates a portion of the undesired heat energy into the environment. This cooling system is managed to permit the engine to operate at the desired temperature, removing some but not all of the heat energy generated by the engine.

As a secondary function, a portion of the heat energy captured by the engine cooling system may be used to indirectly provide warm air as desired to the passenger compartment for the operator's comfort. This recaptured and re-tasked portion of the waste heat energy generated as a byproduct of the engine's primary function represents one familiar example of the beneficial use of waste heat.

Very large internal combustion engines are widely used in heavy industry in numerous applications. For example, General Electric's Jenbacher gas engine division produces a full range of engines with output power capabilities ranging from 250 kW to over 4,000 kW (by comparison, a typical mid-class automobile engine produces about 150 kW of usable output power). The Jenbacher engines can be powered by a variety of fuels, including but not limited to natural gas, biogas (such as provided by anaerobic digestion), and other combustible gasses including those from landfills, sewage, and coal mines. One common use large combustion engines, such as the Jenbacher model 312 and 316 engines, is to co-locate them at a biogas generation facility. This consolidates, at one location, (i) the elimination of biodegradable waste products that release chemical energy in the form of combustible biogas and (ii) the capture and combustion of the biogas in large combustion engines to generate useful power.

These engines are frequently employed to drive electric power generators, converting the rotational mechanical energy from the energy of combustion into electrical energy. One such example of an anaerobic digestion system specifically designed for the generation of electric power from biogas is offered by Harvest Power of Waltham, Mass.

In operation, these engines generate tremendous amounts of waste heat energy that has historically been dissipated into the environment. In the case of the combined Jenbacher model 316 engine and generator system with a maximum electric power output of approximately 835 kW, approximately 460 kW of heat energy is lost in the exhaust gas (at an approximate temperature of 950° F.) and approximately another 570 kW is lost in the cooling system (with a typical jacket water coolant temperature of approximately 200° F.). From this data, it can be seen that less than half of the system's power output is in the desired form (in this case, electric power output from the system generator). Unless recaptured and repurposed, however, the portion of the input energy converted to heat is lost. In many prior art systems, this heat energy is lost and additional energy is required to cool the recirculating jacket water. The heat from exhaust gas generally escapes into the atmosphere, and the recirculating jacket water is cooled by an outboard apparatus (such as by large external condensing radiators driven by forced air sources), which consume additional electric power to function and further reduce the efficiency of the system.

Additionally, the dissipation of this waste heat energy into the environment can have deleterious effects. Localized heating may adversely affect local fauna and flora and can require additional power, either generated locally or purchased commercially, to provide additional or specialized cooling. Further, the noise generated by forced air cooling of the jacket water heat radiators can have undesirable secondary effects.

With regard to engines fueled by anaerobic-digestion-generated biofuel, a variety of techniques, including the use of electrical heating systems, have been employed to provide heat energy to anaerobic digestion processes necessary for relatively efficient generation of biogas by heated microorganisms. These systems consume considerable energy and therefore have an attendant cost of operation and maintenance. For example, the anaerobic digester heating systems offered by Walker Process Equipment of Aurora, Ill. produce hot water in excess of 160° F. using electric power with boilers fueled by biogas, natural gas, or fuel oil as input energy. In addition to the energy consumed to provide this hot water, additional electric energy must be consumed to manage the waste heat from this apparatus.

Waste heat energy systems employing the organic Rankine cycle (ORC) system have been developed and employed to recapture waste heat from sources such as the Jenbacher 312 and 316 combustion engines. One typical prior art ORC system for electric power generation from waste heat is depicted in FIG. 1. Heat exchanger 101 receives a flow of a heat exchange medium in a closed loop system heated by energy from a large internal combustion engine at port 106.

For example, this heat energy may be directly supplied from the combustion engine via the jacket water heated when cooling the combustion engine, or it may be coupled to the ORC system via an intermediate heat exchanger system installed proximate to the source of exhaust gas of one or more combustion engines. In either event, heated matter from the combustion engine or heat exchanger is pumped to port 106 or its dedicated equivalent. The heated matter flows through heat exchanger 101 and exits at port 107 after transferring a portion of its latent heat energy to the separate but thermally coupled closed loop ORC system which typically employs an organic refrigerant as a working fluid. Under pressure from the system pump 105, the heated working fluid, predominantly in a gaseous state, is applied to the input port of expander 102, which may be a positive displacement machine of various configurations, including but not limited to a twin screw expander or a turbine. Here, the heated and pressurized working fluid is allowed to expand within the device, and such expansion produces rotational kinetic energy that is operatively coupled to drive electrical generator 103 and produce electric power which then may be delivered to a local, isolated power grid or the commercial power grid. The expanded working fluid at the output port of the expander, which typically is a mixture of liquid and gaseous working fluid, is then delivered to condenser subsystem 104 where it is cooled until it has returned to its fully liquid state.

The condenser subsystem sometimes includes an array of air-cooler radiators or another system of equivalent performance through which the working fluid is circulated until it reaches the desired temperature and state, at which point it is applied to the input of system pump 105. System pump 105 provides the motive force to pressurize the entire system and supply the liquid working fluid to heat exchanger 101, where it once again is heated by the energy supplied by the combustion engine waste heat and experiences a phase change to its gaseous state as the organic Rankine cycle repeats. The presence of working fluid throughout the closed loop system ensures that the process is continuous as long as sufficient heat energy is present at input port 106 to provide the requisite energy to heat the working fluid to the necessary temperature. See, for example, Langson U.S. Pat. No. 7,637,108 ("Power Compounder") which is hereby incorporated by reference.

As a result of the transfer of waste heat energy from the combustion engine to the ORC system, these types of prior art ORC systems serve two functions. They convert this waste heat energy, which would otherwise be lost, into productive power and they simultaneously provide a beneficial, and sometimes a necessary, cooling or condensation function for the combustion engine. In turn, the ORC system's shaft output power has been used in a variety of ways, such as to drive an electric power generator or to provide mechanical power to the combustion engine, a pump, or some other mechanical apparatus.

ORC systems can extract as much useful heat energy as is practicable from one or more waste heat sources (often referred to as the "prime mover"), but owing to various physical limitations they cannot convert all available waste heat to mechanical or electric power via the expansion process discussed above. Similar in some respects to the cooling requirements of the prime mover, the ORC system requires post-expansion cooling (condensation) of its working fluid prior to repressurization of the working fluid by the system pump and delivery of the working fluid to the heat exchanger. The heat energy lost in this condensation process, however, represents wasted energy which detracts from the overall efficiency of the system.

Some prior art combined prime mover/ORC engine applications have utilized heat generated by the ORC condensation process in a conventional ORC system condenser while simultaneously providing power (electrical and/or mechanical) for various purposes. Combined heat and power ("CHP") ORC systems have typically fulfilled a secondary purpose by using a portion of the heat energy from the prime mover and/or heat energy remaining in the post-expansion working fluid. FIG. 5 depicts a prior art ORC system including combustion engine heat energy output port 501 and condenser heat energy output port 502.

In one prior art ORC application, residual heat extracted from a dedicated ORC condenser during the cooling of post-expansion ORC working fluid at condenser heat energy output port 502 is used to provide domestic hot water, radiant heating, or both. This process requires the use of a conventional ORC condenser system well known in the art. The energy flow of such an application is depicted in the block diagram of FIG. 6. Here, a heat generating engine 601 is operatively coupled to electric generator 602 and provides waste heat energy 603 to the ORC system 604, which is operatively coupled to drive electric generator 605. Heat energy from the prime mover 601 is delivered to heat energy output port 501 and, in some prior art systems, is extracted to (i) a first heat energy input port 606 (such as for radiant heating) and (ii) a second heat energy input port 607 (such as for hot water heating). In those ORC systems known by the applicants, the utilization of residual heat from the post-expansion working fluid is intentionally extracted from the system but is not utilized for further system optimization of the prime mover or, for example, for heating a production material such as microorganisms to generate biofuel.

BRIEF SUMMARY OF SOME ASPECTS OF DISCLOSURE

The applicants have invented apparatus, systems, and methods that productively utilize heat energy generated by ORC working fluid condensation to produce fuel or other power or energy for use by the prime mover. In some embodiments, the prime mover can use the fuel, power, or energy to drive a prime mover.

In certain embodiments, the system includes: (i) a biogas generation system providing combustible biogas to fuel the prime mover; (ii) a prime mover that provides heat energy to drive an ORC engine; and (iii) an ORC engine that provides heat energy to drive the biogas generation system. In some embodiments, the biogas generation system utilizes an anaerobic digestion process which can utilize ORC heat energy to maintain the temperature for the anaerobic process to take place.

In some embodiments, the prime mover may provide mechanical power to drive one or more electric generators. In some embodiments, such generators can be connected to a power distribution grid.

In some applications, the biogas generation system can be co-located with prime mover and ORC system(s) so that (i) one or more prime mover(s) provide waste heat to drive one or more co-located ORC system(s), (ii) one or more ORC system(s) provides waste heat to microorganisms to drive the co-located biogas generation system, and (iii) resulting biogas can provide fuel for one or more co-located prime mover(s). In some of these applications, one or more prime mover(s) and one or more ORC system(s) can simultaneously provide productive power for an of a wide variety of devices and applications, locally or otherwise. Alternatively or in addition, the ORC system(s) may provide waste heat to co-located heat consuming system(s) other than biogas generation system(s). In some applications, the prime mover may receive fuel from more than one source. For example, a prime mover may run on locally-generated biogas during a portion of its operating schedule and another fuel during other portions of its operating schedule. Such other fuels may include but are not limited to stored biogas, biogas imported from other sources, other forms of combustible gasses, or alternate fuels (liquid, solid, or gaseous) suited to the requirements of the prime mover. In some applications, fuels from multiple sources may be mixed together and that mixture supplied to the prime mover. This technique would allow the operator to control the composition of the fact and the exhaust emissions of the prime mover based in its availability and to maximize performance and cost efficiency of its operation.

In some instances, waste heat energy obtained from the exhaust gasses and/or cooling jacket water of the prime mover is provided to one or more ORC system(s) which are operatively coupled to one or more separate electrical generator(s) that are similarly connected to the commercial power distribution grid. The heat coupling subsystem can comprise a heat exchanger which is operatively coupled to provide the requisite condensation of ORC working fluid by transferring heat energy from said fluid to one or more anaerobic digester tank(s). That heat energy can help optimize production of biogas from the anaerobic digestion process used to power the prime mover, and, when operated in concert with an ORC system also generating electric power, improve the efficiency of, and maximize the economic benefit of, the combined system.

The prime mover of some embodiments can be any system, apparatus, or combination of apparatus, that converts some or all of its input energy into heat energy or waste heat energy in a form and quantity sufficient for use by one or more ORC system(s). In some embodiments, the only purpose of the prime mover will be to generate heat for the ORC system(s). All heat energy sources co-located, compatible for use with, and utilized by one or more ORC system(s) fall within the scope of the term "waste heat" for the purpose of this application.

In some systems, a prime mover can generate and deliver mechanical power to an electric power generator in addition to providing waste heat energy for the ORC system(s). In certain embodiments, a prime mover can simultaneously generate more than one form of waste heat, including but not limited to cooling water, hot exhaust gas, or radiated heat. The waste heat energy may be captured and provided to the ORC system in any practicable manner, either directly or via one or more intermediate heat exchanger systems.

In some instances, one or more prime movers may provide waste heat energy to one or more ORC systems. In some embodiments, a single heat exchanger may be employed for any ORC system, any prime mover, any source of heat energy from each prime mover, or for more than one ORC system, prime mover, or heat energy source. These heat exchangers may have separate input ports and separate output ports for the energy source(s) or a single input and/or output port may be utilized for more than one source.

In certain embodiments, one or more ORC system(s) operate with a closed loop refrigerant cycle to prevent intermixture of working fluid between systems. Similarly, in some instances one or more prime mover(s) operate with a closed loop jacket water cooling system to prevent any intermixture of jacket water between systems. In other embodiments, a single exhaust gas heat recovery system is employed to recover waste heat energy from more than one prime mover and provide such heat energy to more than one associated ORC system. In some embodiments, a heat recovery system receives heat energy input from one or more sources and/or provides heat energy to more than one ORC system.

In some systems, one or more additional heat sources provide heat input to the ORC system(s). For example, a portion of the biogas generated by the anaerobic digestion process may be burned a separate boiler and used to provide heat input to the ORC system(s) in addition to, or in lieu of, waste heat input from one or more prime mover(s).

In certain embodiments, a portion of the waste heat energy from the prime mover may be applied directly to the anaerobic digestion process without having been first applied to the ORC system(s). This can be beneficial in the event that the anaerobic digestion heating requirements exceed the residual heat energy available from the post-expansion working fluid in the ORC system(s).

In some applications, one or more ORC systems constitute the entire jacket water cooling system for the prime mover(s). In such cases, the ORC systems may replace alternative prime mover cooling systems, which consume, rather than generate, power during operation and therefore usually have a significant cost of operation in addition to their cost of installation. Such power consuming dedicated prime mover cooling systems typically have a significantly larger footprint than an ORC system; and therefore they may have additional physical space requirements at the generation facility. They may also generate noise and unwanted environmental heat pollution as a consequence of operation. Employing one or more ORC system(s) in lieu of power consuming dedicated prime mover cooling systems, which are net consumers of power under such circumstances, can be economically, physically, and environmentally beneficial.

In some embodiments, the waste heat recovery system(s) include one or more power generating system, which may be ORC system(s), and one or more power receiving component(s), which may be but are not limited to electric power generator(s), prime mover(s), pump(s), combustion engine(s), fan(s), turbine(s), compressor(s), and the like. The rotational mechanical power generated by the power generating system(s) is delivered to the power receiving components.

In some embodiments, the ORC system(s) provide a portion of the cooling system for the prime mover(s) and operate in conjunction with one or more additional cooling system(s). In some embodiments, electric power generated by the ORC systems may be applied to the operation of said additional cooling systems for the prime mover as well as provide electric power for other purposes at the site or elsewhere. This can be particularly advantageous if, for example, the prime mover is configured to solely provide mechanical power output and a commercial source of electric power is not readily available.

In some embodiments, one or more ORC system(s) may provide heat energy to one or more anaerobic digestion tanks or other anaerobic digestion structure. In some instances, multiple ORC systems can provide heat energy to a single anaerobic digestion tank. In some embodiments, the anaerobic digestion heating system includes the entire condenser subsystem for the ORC system(s). In other embodiments, the anaerobic digestion heating system comprises a portion of the ORC condenser subsystem(s) in combination with one or more other condensing system(s) which may operate on a regular or intermittent basis dictated by a number of factors including seasonal requirements. The ambient environmental conditions, the number of ORC systems and their ratings, and/or the number, configuration, location, or volume of the anaerobic digestion tanks may each be factors in determining the configuration and operation of the condenser portion of the ORC systems.

In some embodiments, the heat energy supplied by the ORC system to the anaerobic digestion process can reduce or even completely obviate the need for a supplemental anaerobic digestion tank heating system. In some instances, this can reduce or even eliminate the cost of installation, maintenance, and operation of such supplemental system, including costs associated with electric power and/or other fuels which may have previously been consumed by its operation. In some cases, the ORC system can provide heat to the anaerobic digestion process in combination with one or more other heating systems, which can serve to reduce rather than eliminate the attendant costs.

In some embodiments, the ORC system supplies all heat required by the anaerobic digestion system via the transfer of heat energy from the ORC process. In some embodiments, some or all of the electric power generated by the ORC system can be supplied to electrical heating systems to heat the anaerobic digestion tank(s). This heating can be in addition to, or in lieu of, the direct transfer of heat energy from the ORC system to the anaerobic digestion system and can vary based on factors such as the availability of heat enemy and/or other electrical power, heating requirements, and the like. In some embodiments, a portion of electric power output generated by the ORC system is supplied to other components or systems operatively connected (either electrically, mechanically, or thermally) to the combined ORC and anaerobic digestion system, including but not limited to other heating systems, cooling systems, fans, pumps, compressors, circulation systems, filtration equipment, stirring systems, and the like.

The foregoing is a brief summary of only some of the novel features, problem solutions, and advantages variously provided by the various embodiments. It is to be understood that the scope of the invention is to be determined by the claims as issued and not by whether a claim addresses an issue noted in the Background or provide a feature, solution, or advantage set forth in this Brief Summary. Further, there are other novel features, solutions, and advantages disclosed in this specification; they will become apparent as this specification proceeds.

BRIEF DESCRIPTION OF THE DRAWINGS

Without limiting the invention to the features and embodiments depicted, certain aspects this disclosure, including the preferred embodiment, are described in association with the appended figures in which.

DETAILED DESCRIPTION OF THE PREFERRED AND OTHER EMBODIMENTS

The process of anaerobic digestion is well known in the art. Certain strains of bacteria, in the absence of oxygen, are employed to break down, or digest, certain biodegradable material including food, yard, or other waste into combustible gasses consisting of methane, hydrogen, and other trace components, as well as a residual solid effluent. This effluent, or sludge, contains ammonia, phosphorous, potassium, and other trace materials and is beneficial to agriculture as a supplemental enrichment fertilizer for soil.

The anaerobic digestion process involves three basic stages involving different microorganisms, and the temperature of the cultures can play a very significant role in the efficiency of the digestion process. Mesophilic digestion, occurring at medium temperatures, can be applied to discrete batches of biodegradable waste while thermophilic digestion, occurring at higher temperatures, may preferably be utilized on a continuous basis. Although the anaerobic digestion microorganisms can survive within the range from below freezing to above 135° F. optimal digestion occurs at 98° F. for mesophilic organisms and 130° F. for thermophilic organisms. Bacterial activity and therefore biogas production is significantly reduced at greater temperatures and declines at a somewhat lesser rate at cooler temperatures. The requirement for heating of the cultures may vary over time (over the course of a single day and, as seasons change, throughout the year) based on ambient temperatures.

Figure 1:
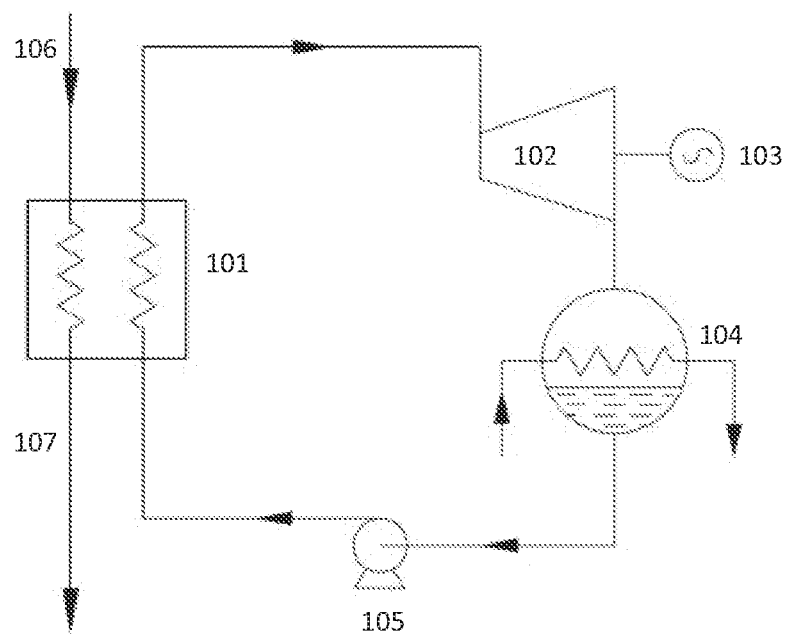
FIG. 1 is a block diagram of a prior art ORC system used to convert waste heat energy into electric power.
Figure 2A:
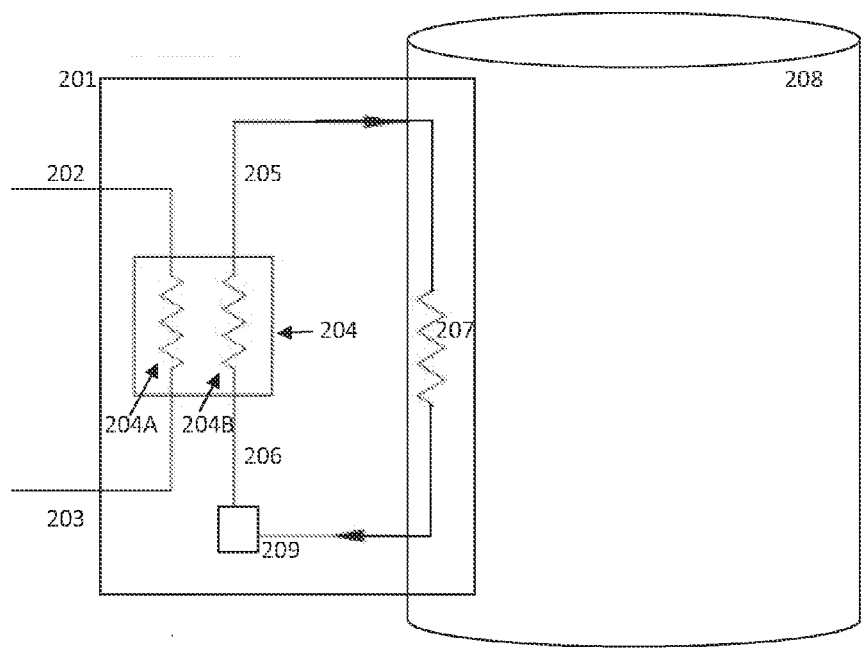
FIG. 2A is a block diagram of a heat coupling subsystem with heat exchangers to transfer heat energy from a closed loop system to an anaerobic digestion tank.

With reference now to FIG. 2A, a heat coupling subsystem 201 can be used to transfer heat energy to the anaerobic digestion process while maintaining media isolation between a heat source and an anaerobic digestion system in the heating tank 208, owing to potentially different media requirements of the two systems. The heat coupling subsystem 201 includes (i) an intermediate heat exchanger 204, (ii) an anaerobic digestion tank heat exchanger 207 within, as part of the wall of, or otherwise in direct thermal communication with, the anaerobic digestion tank 208, (iv) pumping apparatus 209 between the tank heat exchanger 207 and the intermediate heat exchanger 204, (v) operative coupling between the various components described below, and (vi) secondary media (which may be the same as or different from the primary medium depending on system requirements) flowing within the isolated closed loop provided by the tank-side (secondary) portion of the heat coupling subsystem 201 via the input port 206 and the output port 205, the anaerobic digestion tank heat exchanger 207, and the pumping apparatus 209. Heat coupling subsystem 201 may also include storage reservoirs (not shown) for a quantity of both the primary medium and the secondary medium as necessary to insure that sufficient media is available for the proper operation of each closed loop systems on the primary and secondary sides.

The primary side of the intermediate heat exchanger 204 includes a primary side input port 202 to receive the heated primary media (not shown) from the heat source, which may be an ORC system, a prime mover, or any other source of heat energy, a primary side heat exchanger section 204A, and a primary side output port 203. This flow provides heat energy from the ORC system for transfer to, and use by, the anaerobic digestion tank(s), e.g., 208. The heated primary media can be ORC working fluid, water, a mixture of water and ethyl glycol, a mixture of water and one or more other components, or any other fluid or gaseous substance compatible with the application and apparatus. The heated primary media passes through the primary side 204A of intermediate heat exchanger 204 and exits at primary side exit port 203. Heat energy from the heated primary media is transferred to the secondary side of the intermediate heat exchanger 204, through which a suitable secondary media (not shown) enters at secondary side input port 206, flows through secondary side heat exchanger section 204B, and exits at secondary side output port 205. This heated secondary media then flows through anaerobic digestion tank heat exchanger 207, where heat energy is transferred from the heated secondary media to the contents of anaerobic digestion tank 208 before being pressurized by pumping apparatus 209 and returned to secondary side of the intermediate heat exchanger 204 at the secondary side input port 206.

Figure 2B:
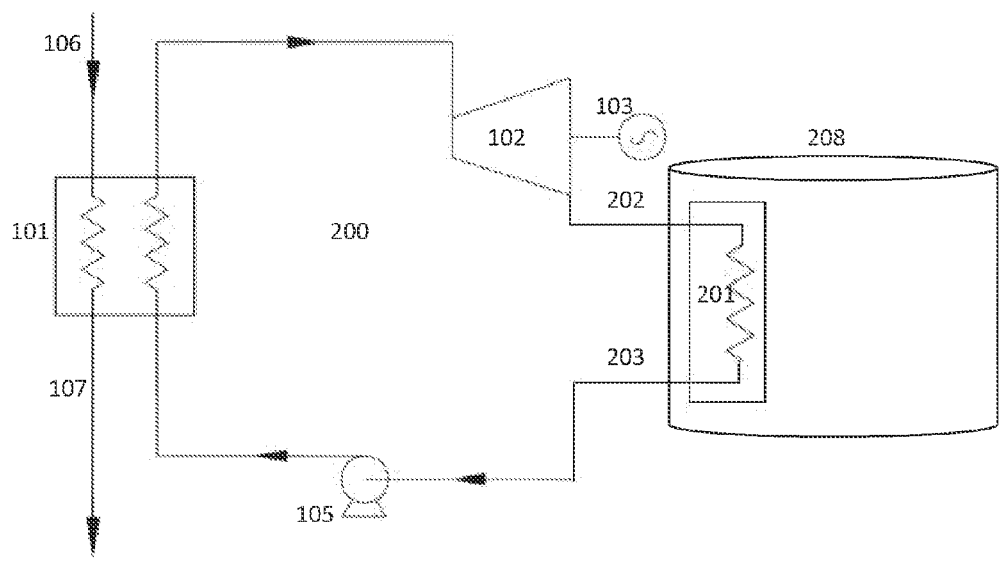
FIG. 2B is a block diagram of a single ORC system used to convert waste heat energy into electric power while simultaneously providing heat energy to a single anaerobic digestion tank that provides condensing functionality for the ORC system.

With reference now to FIG. 2B, an ORC system, generally 200, utilizes the heat coupling subsystem 201 within, as part of the wall of, or otherwise in direct thermal communication within anaerobic digestion tank 208 to provide cooling for the post-expansion working fluid exiting from the expander 102. The ORC working fluid exits the expander 102 and enters input port 202, travels through the heat coupling subsystem 201, and then exits the output port 203 and enters the system pump 105. The heat coupling subsystem 201 and anaerobic digestion tank 208 therefore provide an integrated working fluid condensation and heat consumption system. That is, the anaerobic digestion tank heat exchanger 207, when coupled to the ORC system via intermediate heat exchanger 204 in the manner shown in FIG. 2A and described in detail above, comprise heat coupling subsystem 201 which may be considered to function as a single heat exchanger for the purposes of the ORC system. Analogous to the performance of a transformer in an electrical system, heat coupling subsystem 201 serves as a "thermal transformer" which transfers heat energy from its primary (ORC) side to its secondary (tank) side while maintaining isolation between the separate media flowing in each closed loop. This provides the equivalent performance of a condenser known in the prior art with significant improvements. This particular system is also a production system, meaning that the heat coupling subsystem 201 provides heat energy, via anaerobic digestion tank heat exchanger 207, directly for production and not for mere disposition of the heat as waste. In this example, the anaerobic digestion tank heat exchanger 207 directly heats the contents of the anaerobic digestion tank 208, yielding production of biogas. The temperature of the post-expansion working fluid entering input port 202 should be about 125° F., which is nearly ideal for the purpose of supplying heat to a continuous mesophilic anaerobic digestion process including the heat energy losses from an intervening intermediate heat exchanger.

Referring to both FIGS. 2A and 2B, in an embodiment utilizing an intermediate heat exchanger 204, less heat energy will be delivered to the anaerobic digestion tank(s) than is provided to the primary side, i.e., through input port 202, of heat coupling subsystem 201 due to the unavoidable loss of heat energy during the heat transfer process from the primary medium to the secondary medium via intermediate heat exchanger 204. However, for applications with reduced anaerobic digestion heating requirements, such as mesophilic digestion processes, this loss of heat energy can be beneficial and can eliminate the requirement for a dedicated supplemental condensing apparatus. This method may be applied to any configuration of the anaerobic digestion heating apparatus.

Figure 2C:
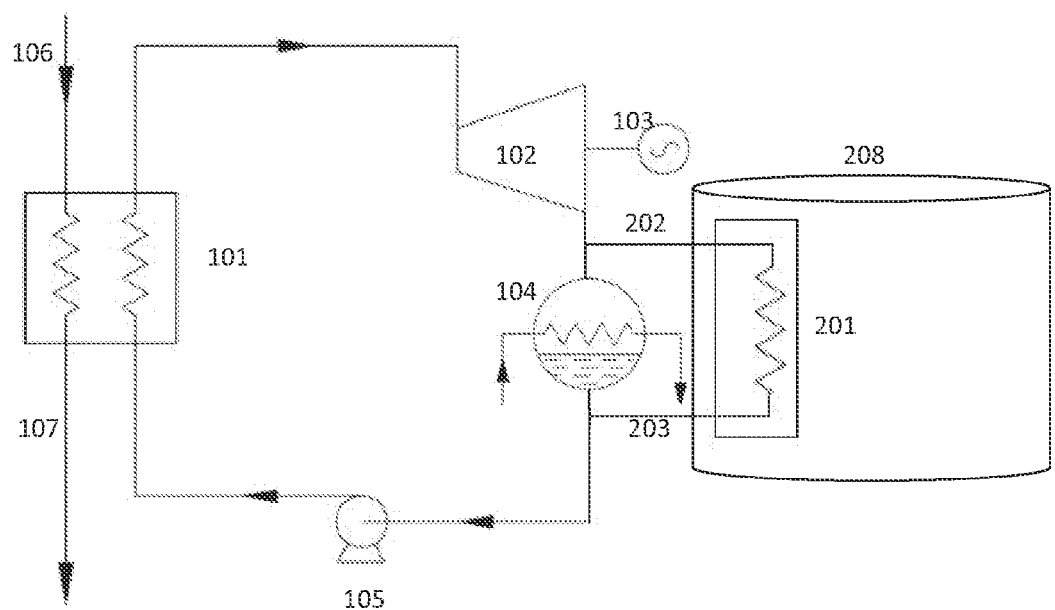
FIG. 2C is a block diagram of a single ORC system used to convert waste heat energy into electric power while simultaneously providing heat energy to a single anaerobic digestion tank that provides partial condensing functionality for the ORC system, augmented by the presence of a separate condenser.

With reference now to FIG. 2C, the structure and operation of the system is identical to that of FIG. 2B with the addition of an ORC condenser subsystem 104 between the input port 202 and the outlet port 203. Post-expansion ORC working fluid can thus travel through either or both (i) the condenser subsystem 104 and (ii) the heat coupling subsystem 201 associated with the anaerobic digestion tank 208. This embodiment may be used when insufficient condensing capacity might be provided by the anaerobic digestion tank 208 or during periods of ORC operation when the anaerobic digestion tank 208 is not in service.

Figure 3:
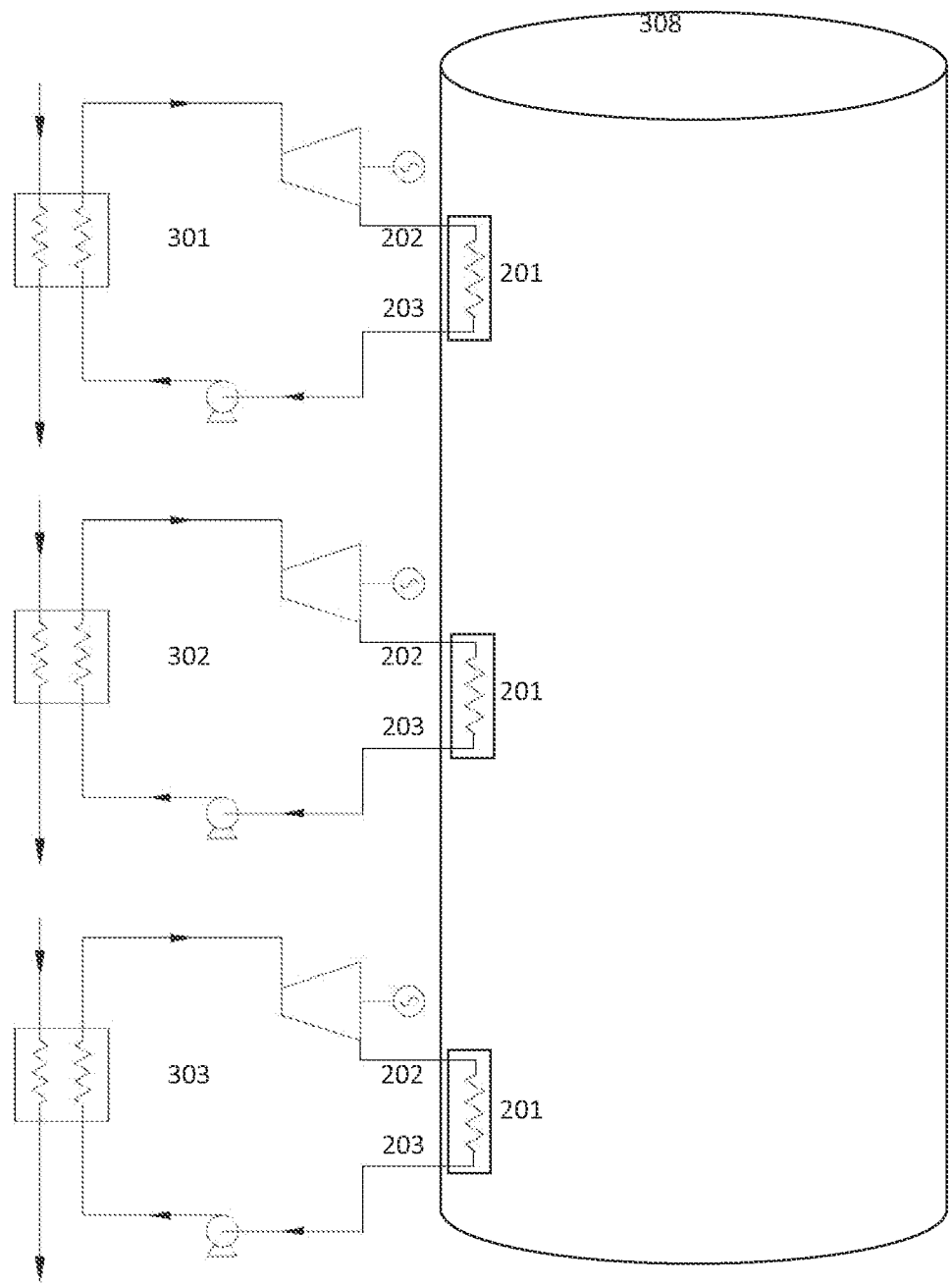
FIG. 3 is a block diagram of multiple ORC systems simultaneously delivering heat energy to a single anaerobic digestion tank while providing condensing functionality for the ORC systems.

With reference now to FIG. 3, a series of ORC systems 301, 302, 303 are combined to provide heat energy to an anaerobic digestion tank 308. Although three ORC systems are depicted, any number of ORC systems can be included to provide the desired level of heat transfer to the anaerobic digestion tank 308. This embodiment may be particularly advantageous for large anaerobic digestion facilities in order to maintain a uniform temperature throughout a large volume anaerobic digestion tank 308. Since the temperature of the medium circulating within the anaerobic digestion heating system can be higher at its point of entry into the tank and generally lowest at its point of exit as the heat energy is transferred to the contents of the tank, the introduction of several independent ORC systems, e.g., 301, 302, 303 at different locations in the anaerobic tank 308 can provide for a more even distribution of heat and corresponding uniform temperature than would be possible from a single source.

The same or similar result may be achieved by a single ORC system (not shown) using a specially designed manifold system (not shown) having multiple heat coupling subsystems 201. For larger digestion tanks, however, the finite heat energy available from a single ORC system may be insufficient to maintain the temperature of the tank contents uniformly at its desired, and in some instances, optimal value. Any configuration of heat coupling subsystems 201 may be employed to provide optimal results.

In order to provide the desired results, the geometry and configuration of an anaerobic digestion tank heat exchanger 201 used to simultaneously heat the contents of the anaerobic digestion tank(s) and provide condensation of the post-expansion working fluid can be designed and implemented in view of the desired performance of both subsystems. In one embodiment, the heated medium (the post-expansion working fluid) flowing within the anaerobic digestion tank heat exchanger 201 may directly circulate within a series of interconnected pipes and/or manifolds (not shown) inside the anaerobic digestion tank(s). These structures can be essentially planar with media flows in a single plane (neglecting the thickness of the components) or may be more three dimensional with heated medium flows in two or more planes. The configuration of the anaerobic digestion tank heat exchanger 201 may be designed with, as shown in FIGS. 2B and 2C, a single input port 202 and output port 203 or may be configured with, as shown in FIG. 3, multiple input ports 202 and output ports 203 to provide a more uniform distribution of heat throughout the anaerobic digestion tank 308. Further, the interconnected pipes and/or manifolds may include a series of valves that permit control and redirection of the heated medium to various regions of the anaerobic digestion tank 308 as may be desired to achieve the preferred distribution of heat. In another embodiment, the heated medium may circulate through sealed channels embedded in the walls of the anaerobic digestion tank(s), thereby heating the contents of the tank at its interior boundaries or side wall(s).

Figure 4:
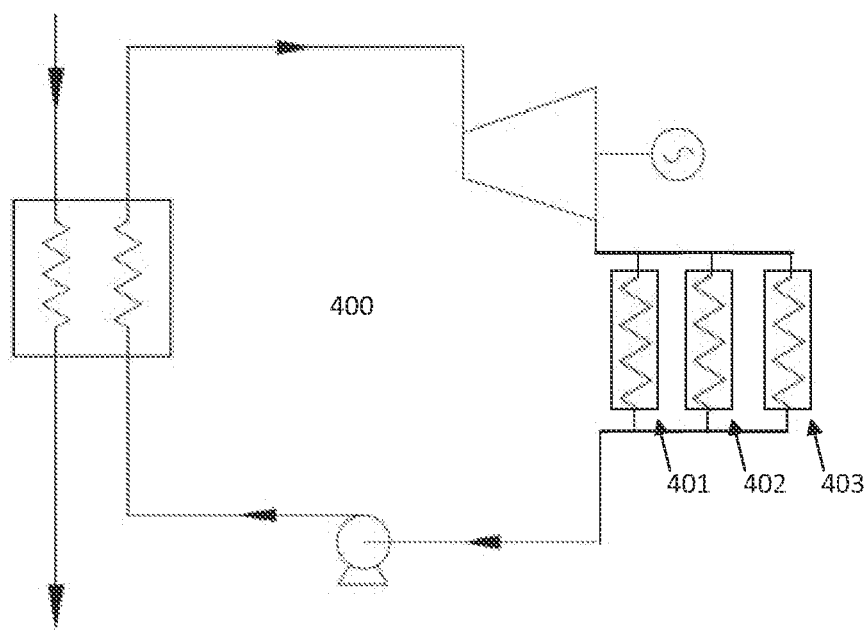
FIG. 4 is a block diagram of a single ORC system simultaneously delivering heat energy to a multiple anaerobic digestion tanks while providing condensing functionality for the ORC system.
Figure 5:
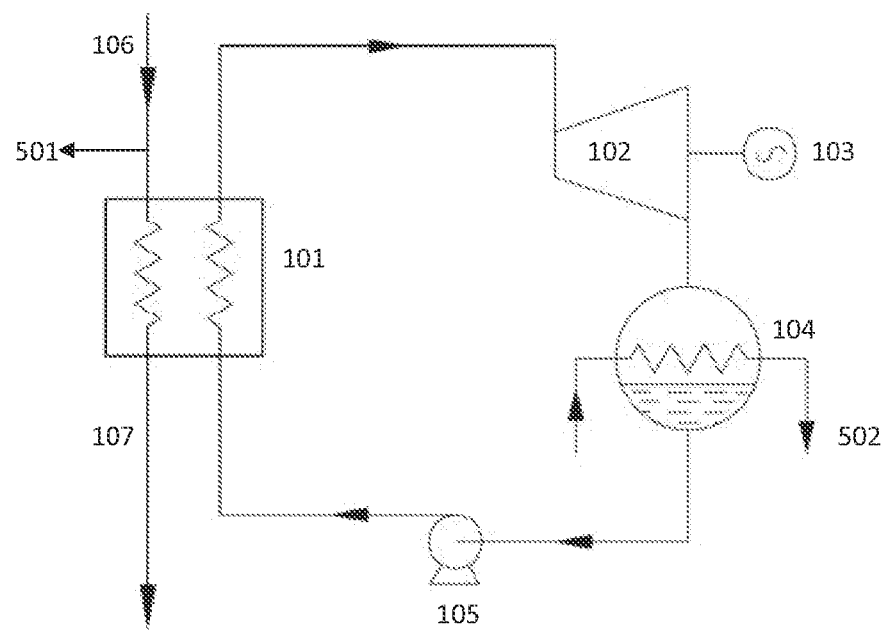
FIG. 5 is a block diagram of a prior art ORC system used to convert waste heat energy into electric power including heat extraction ports that can be used to provide heat for other applications.
Figure 6:
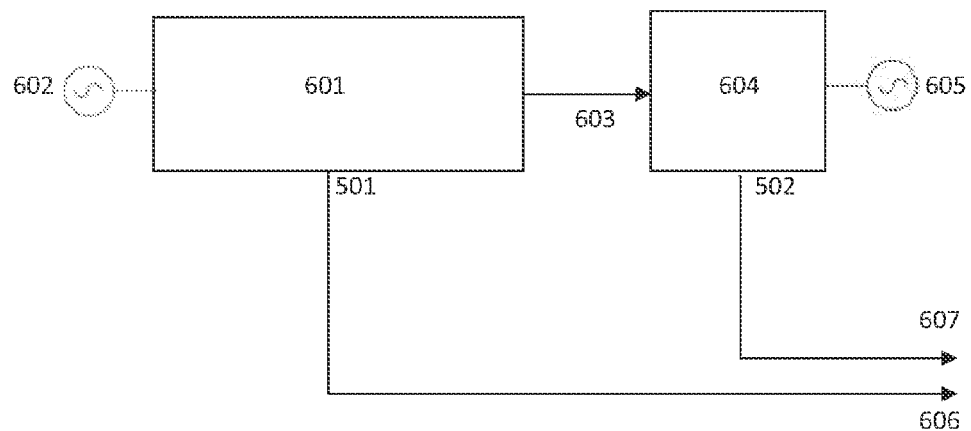
FIG. 6 is a block diagram of the energy flow in a prior art system comprising a prime mover, an ORC system used to convert waste heat energy into electric power, and heat extraction ports for other non-system applications.

With reference now to FIG. 4, a single ORC system 400 may be used to provide heat energy to more than one anaerobic digestion tank (not shown) via multiple heat coupling subsystems 401, 402, and 403. In this embodiment, the available heat energy from post-expansion working fluid from an ORC system 400 is distributed to anaerobic digestion tank heat exchangers (not shown) in each of three discrete anaerobic digestion tanks (not shown) via heat coupling subsystems 401, 402, and 403. Each of these heat coupling subsystems 401, 402, 403 may be comparable to heat coupling subsystem 201 shown in FIG. 2A. The specific distribution of post-expansion working fluid provided to each heat coupling subsystem 401, 402, 403 can be controlled, varying it as needed to allocate the available heat energy among the several tanks. In some instances, this method can be well suited for smaller tanks, systems with reduced requirements for anaerobic digestion heating, or lower temperature mesophilic batch processing, particularly where not all tanks are in simultaneous use. Although three tanks are referenced here, any number of tanks are envisioned that provide the requisite performance.

These combined ORC and anaerobic digestion systems are distinguished from known prior combined heat and power systems in that the prior technology merely siphons some portion of heat energy from ports added to known ORC systems. The known prior art does not teach, for example, the replacement of ORC condenser systems, in whole or in part, with an alternate system including one that simultaneously provides, via one heat coupling subsystem: (i) heating directly to a heat consuming process which provides some beneficent function and (ii) an equivalent cooling and condensation function for the ORC working fluid primary media, which may be heated post-expansion working fluid from the ORC. In this regard, known prior art ORC systems typically require significant electric power to drive fans or an equivalent cooling system. The economic advantage of generating power from waste heat energy is greatly reduced when a large portion of the generated power is consumed by the system's internal requirements (sometimes referred to as the "parasitic load"). The combined ORC and anaerobic digestion system thus provides a double economic advantage; not only is the requisite cooling provided for the primary media, which in the case of an ORC will be heated post-expansion working fluid, without additional electric power consumption, but the electric power normally required to maintain the anaerobic digestion tanks at the optimal temperature is no longer required due to the transfer of heat energy from the companion ORC system. While the known prior art requires electric power to simultaneously cool the ORC media and heat the anaerobic digestion tanks, the combined ORC and anaerobic digestion system reduces or eliminates both requirements for electric power by transferring unwanted heat energy directly via heat coupling subsystem 201 from the ORC system to the anaerobic digestion system. As a result, the net electric power generated by the combined ORC and anaerobic digestion system is significantly greater than in the present art, providing greater economic benefit while conserving resources necessary to produce electric power.

In some embodiments of the present application, anaerobic digestion-based biogas power generation systems can be enhanced by integrating the functions of an ORC waste heat energy generation system with the biogas-burning prime mover and the anaerobic digestion process which generates the biogas for the prime mover. Both the heat input and heat output of the ORC system can be coupled to other components within the overall system. Unlike the known prior art, which does not integrate all three subsystems into a single optimized energy conversion system, some embodiments of the present application provide for increased and possibly maximum efficiency by utilizing more and possibly all available heat energy within the system to a greater, and possibly the greatest, extent practicable.

In certain embodiments, no heat energy is intentionally dissipated or redirected to any non-system application. In certain instances, as some or all of the lowest grade residual waste heat energy remaining after two stages of electric power generation is returned to enhance, and in some instances optimize, the production of fuel for the primary electric power generation process, the system forms a novel and more effective three stage closed-energy-loop.

More specifically, the novel combined prime mover, ORC, and anaerobic digestion system taught herein uniquely allows for each of the three component systems to provide operational benefits of the other two. Specifically, the anaerobic digestion system can, in certain embodiments, be the anaerobic digestion system offered by Harvest Power as described above. In certain embodiments, the prime mover(s), which can be the Jenbacher 312 or 316 internal combustion engines also described above, are fueled by biogas produced by the anaerobic digestion process and cooled, in whole or in part, by one or more ORC system(s) which remove undesired waste heat energy and convert it to useful mechanical and/or electrical power. In this manner, the ORC system(s), which in certain embodiments can be Series 4000 Green Machine ORC system(s) offered by ElectraTherm. Inc. of Reno, Nev., receive their input energy in the form of waste heat from the prime mover(s) and provide post-expansion heat energy to the anaerobic digestion process to enhance the production of biogas fuel for the prime mover(s). Additionally, the heat energy from the ORC that is absorbed by the anaerobic digestion process system provides the necessary cooling condensation of post-expansion ORC working fluid, obviating the need for a separate OCR condenser and the attendant cost of operation. As each of the three component system enhance the operation of the other two, all available heat energy is utilized to the greatest extent possible and the need for additional energy, particularly electrical energy, to provide cooling and/or heating as in the present art is minimized or eliminated.

Figure 7:
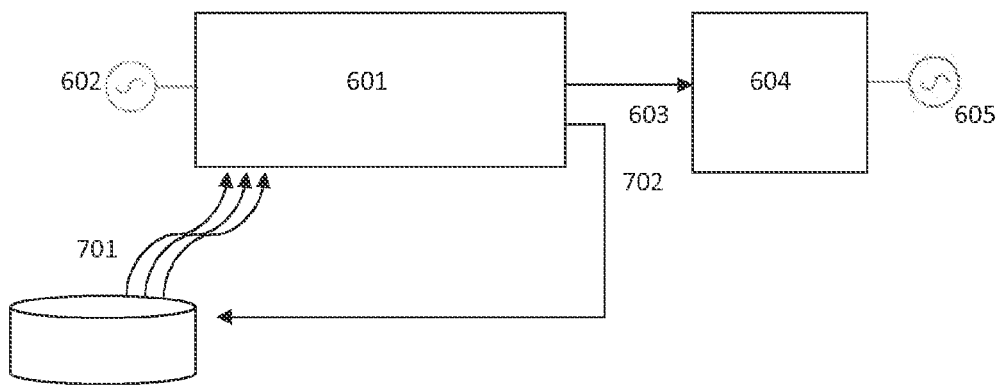
FIG. 7 is a block diagram of the energy flow in a system comprising a prime mover, an ORC system used to convert waste heat energy into electric power, and heat extraction from the prime mover used to improve system efficiency.

In one embodiment depicted in FIG. 7, the prime mover 601 can simultaneously contribute heat energy and/or waste heat energy 603 to the ORC system 604 and heat energy 702 to the anaerobic digestion tank 701, which provides the biogas fuel for the prime mover 601.

Figure 8:
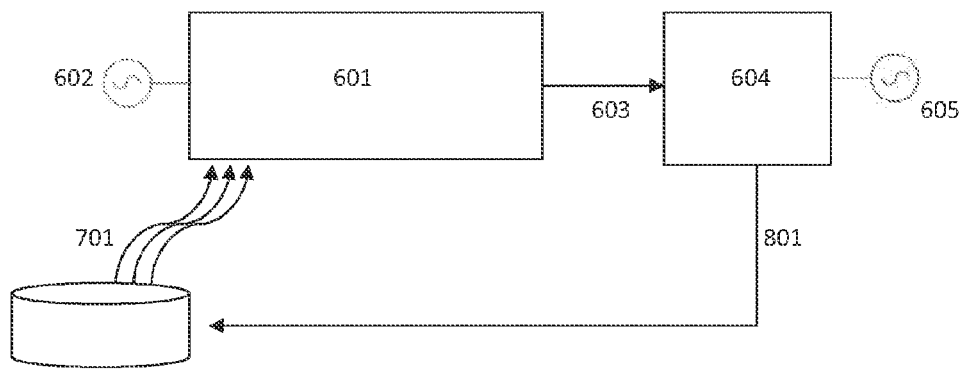
FIG. 8 is a block diagram of the energy flow in a system comprising a prime mover, an ORC system used to convert waste heat energy into electric power, and heat extraction from the ORC system used to improve system efficiency.

In an embodiment depicted in FIG. 8, the ORC system 604 can obtain its heat input from the waste heat energy 603 of prime mover 601 and deliver its own waste heat energy 801 to the anaerobic digestion process. Heat energy flow 801 may be provided from the post-expansion working fluid to anaerobic digestion tank 701.

Figure 9:
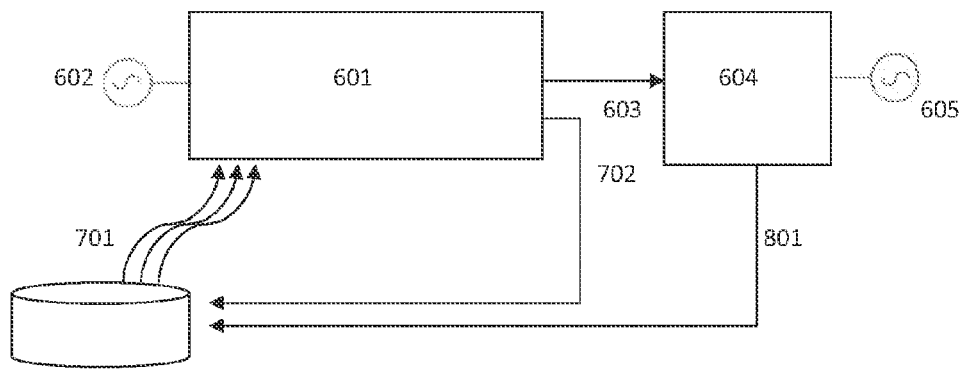
FIG. 9 is a block diagram of the energy flow in a system comprising a prime mover, an ORC system used to convert waste heat energy into electric power, and heat extraction from the prime mover and from ORC system used to improve system efficiency.

In an embodiments depicted in FIG. 9, both the prime mover 601 and the ORC system 604 provide heat energy to anaerobic digestion tank 701 as depicted in FIG. 9 via heat flows 702 and 801, respectively.

Figure 10:
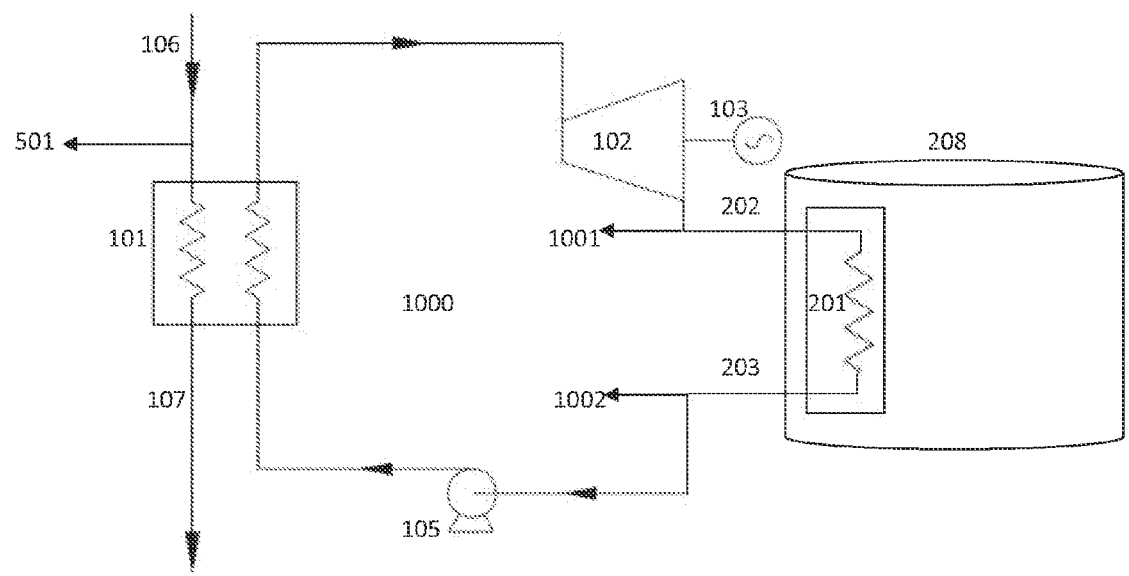
FIG. 10 is a block diagram of a single ORC system used to convert waste heat energy into electric power while simultaneously providing heat energy to a single anaerobic digestion tank that provides condensing functionality for the ORC system, including heat extraction ports that can be used to provide heat for other applications.

In addition to the heat energy being transferred from the primary media (which in some embodiments may be post-expansion ORC working fluid) to the anaerobic digestion process to increase the efficiency of the overall system, heat energy may also be extracted for other purposes. With reference now to FIG. 10, a prime mover (not shown in FIG. 10) can provide heated prime mover media to the heat exchanger 101 of an ORC system 1000 and to a prime mover heat energy output port 501. Post-expansion working fluid heat energy can be provided to the anaerobic digestion tank heat exchanger 201 and to an output port 1001; and post-anaerobic digestion tank heat exchanger heat energy can be provided to output port 1002. Any combination of these ports may be utilized to provide heat energy for one or more purposes not related to the operation of the CHP system.

In addition to anaerobic digestion systems, any application benefiting from significant heat energy may be similarly integrated with an ORC system as a heat receiving system with condensation capacity in the manner taught herein. The anaerobic digestion tank(s) function as a single subsystem providing combined working fluid condensation and the consumption of heat energy for beneficent use. As with the heating of anaerobic digestion tank(s), any application in which coupled heat energy from the primary media may replace the generation of heat energy via the consumption of electric power will operate with greater efficiency and economic benefit and may serve as a heat receiving system with condensation capacity. Such applications may include but are not limited to the heating of water in swimming pools, preheating water for boiler systems, space heating, industrial or large scale domestic hot water systems, combined heat and power systems, and the like. As a result, these systems will also provide the dual benefit of providing heat energy normally produced by electric power while simultaneously eliminating the need for a separate ORC cooling and condensing system in the present art.

In some embodiments where insufficient cooling and condensation functionality may be available from the anaerobic digestion system for proper operation of the ORC, a supplemental or alternate system may be required if it is desirable to run the ORC. In some embodiments, the ORC may serve as a primary cooling system for the prime mover(s). The description of this invention is intended to be enabling and not it will be evident to those skilled in the art that numerous combinations of the embodiments described above may be implemented together as well as separately, and all such combinations constitute embodiments effectively described herein.

The invention claimed is:

1. A waste heat recovery system comprising in combination:
   A. a supply of waste heat energy from a prime mover heat generating component of a prime mover;
   B. at least one prime mover fuel source including an anaerobic digestion system in prime mover fuel transfer sending communication with the prime mover;
   C. a power receiving component; and
   D. a power generating system having:
      i. a system pump,
      ii. an evaporator in working fluid transfer communication with the system pump and in heat transfer communication with the prime mover heat generating component,
      iii. a working fluid expander (a) in working fluid transfer communication with the evaporator and (b) in mechanical power delivery communication with the power receiving component, and
      iv. a closed loop working fluid heat removal and condensing subsystem having (a) an ORC working fluid input in working fluid communication with the working fluid expander outlet, (b) an ORC working fluid output in working fluid communication with the system pump inlet, and (c) separate secondary heat transfer media in separate closed loop thermal transfer communication with the working fluid and the at least one prime mover fuel source;
   wherein the system is configured in closed-loop energy transfer communication such that
      a) prime mover fuel is provided from the at least one prime mover fuel source to the prime mover,
      b) prime mover fuel is consumed by the prime mover heat generating component of the prime mover,
      c) heat generated by said prime mover heat generating component is provided to the power generating system, and
      d) heat removed from the working fluid in the working fluid heat removal and condensing subsystem of the power generating system is provided to the at least one prime mover fuel source for use in the production of prime mover fuel.

2. The waste heat recovery system of claim 1 wherein the power receiving component comprises an electric generator.

3. The waste heat recovery system of claim 2 wherein the working fluid expander comprises a screw expander in rotational power delivery communication with the power receiving component.

4. The waste heat recovery system of claim 2 wherein the working fluid expander comprises a twin screw expander in rotational power delivery communication with the power receiving component.

5. The waste heat recovery system of claim 2 wherein the power generating system includes a closed loop organic Rankine cycle system comprising the system pump, the evaporator, the working fluid expander, and the working fluid heat removal and condensing subsystem.

6. The waste heat recovery system of claim 1 wherein the power receiving component includes one or more among a pump, a combustion engine, a fan, a turbine, or a compressor.

7. The waste heat recovery system of claim 6 wherein the working fluid expander comprises a screw expander in rotational power delivery communication with the power receiving component.

8. The waste heat recovery system of claim 6 wherein the working fluid expander comprises a twin screw expander in rotational power delivery communication with the power receiving component.

9. The waste heat recovery system of claim 6 wherein the power generating system includes a closed loop organic Rankine cycle system comprising the system pump, the evaporator, the working fluid expander, and the working fluid heat removal and condensing subsystem.

10. The waste heat recovery system of claim 1 wherein a rotating element of the working fluid expander is in rotational power delivery communication with a rotating element of the power receiving component.

11. The waste heat recovery system of claim 10 wherein the working fluid expander comprises a screw expander.

12. The waste heat recovery system of claim 10 wherein the working fluid expander comprises a twin screw expander.

13. The waste heat recovery system of claim 10 wherein the power generating system includes a closed loop organic Rankine cycle system comprising the system pump, the evaporator, the working fluid expander, and the working fluid heat removal and condensing subsystem.

14. The waste heat recovery system of claim 1 wherein the at least one prime mover fuel source includes a biogas source.

15. The waste heat recovery system of claim 14 wherein the working fluid expander comprises a screw expander in rotational power delivery communication with the power receiving component.

16. The waste heat recovery system of claim 14 wherein the working fluid expander comprises a twin screw expander in rotational power delivery communication with the power receiving component.

17. The waste heat recovery system of claim 14 wherein the power generating system includes a closed loop organic Rankine cycle system comprising the system pump, the evaporator, the working fluid expander, and the working fluid heat coupling removal and condensing subsystem.

18. The waste heat recovery system of claim 1 wherein the working fluid heat removal and condensing subsystem includes a water heating component.

19. The waste heat recovery system of claim 1 wherein the working fluid expander comprises a screw expander in rotational power delivery communication with the power receiving component.

20. The waste heat recovery system of claim 19 wherein the power generating system includes a closed loop organic Rankine cycle system comprising the system pump, the evaporator, the working fluid expander, and the working fluid heat removal and condensing subsystem.

21. The waste heat recovery system of claim 1 wherein the working fluid expander comprises a twin screw expander in rotational power delivery communication with the power receiving component.

22. The waste heat recovery system of claim 21 wherein the power generating system includes a closed loop organic Rankine cycle system comprising the system pump, the evaporator, the working fluid expander, and the working fluid heat removal and condensing subsystem.

23. The waste heat recovery system of claim 1 wherein the power generating system includes a closed loop organic Rankine cycle system comprising the system pump, the evaporator, the working fluid expander, and the working fluid heat removal and condensing subsystem.

24. A waste heat recovery method using a prime mover in prime mover fuel transfer receiving communication with at least one prime mover fuel source including an anaerobic digestion system, said method comprising;

A. directing heat produced in said prime mover to an input of a waste heat recovery system;
B. transferring thermal energy from said heat to an evaporator in the waste heat recovery system;
C. generating heated working fluid in the evaporator;
D. directing said heated working fluid from the evaporator through an expander and converting energy in the heated working fluid into mechanical energy as said heated working fluid flows through said expander;
E. transferring at least a portion of the converted mechanical energy from the expander to a power receiving component;
F. transferring said heated working fluid from the expander to a working fluid heat removal and condensing subsystem and, in the working fluid heat removal and condensing subsystem, generating cooled working fluid liquid and heated separate secondary heat transfer media;
G. transferring said cooled working fluid liquid from the working fluid heat removal and condensing subsystem to the evaporator;
H. circulating said separate secondary heat transfer media in a separate closed loop within the working fluid heat removal and condensing subsystem to transfer heat from the working fluid to said at least one prime mover fuel source including an anaerobic digestion system;
I. directing thermal energy from said separate secondary heat transfer media in the separate closed loop to said at least one prime mover fuel source to generate prime mover fuel;
J. directing prime mover fuel from the at least one prime mover fuel source to the prime mover; and
K. using said prime mover fuel to provide power to the prime mover so as to create heat that is directed to the input of the waste heat recovery system.

25. The waste heat recovery method of claim 24 wherein the method includes operating a closed loop Rankine cycle comprising Steps C, D, F, and G.

26. The waste heat recovery method of claim 25 wherein the power receiving component comprises an electric generator.

27. The waste heat recovery method of claim 25 wherein the power receiving component includes one or more among the prime mover, a pump, a combustion engine, a fan, a turbine, or a compressor.

28. The waste heat recovery method of claim 25 wherein the directing step (I) includes directing the thermal energy from said separate secondary heat transfer media in the separate closed loop to a prime mover biogas fuel source.

29. The waste heat recovery method of claim 25 wherein the directing step (I) includes directing the thermal energy from said separate secondary heat transfer media in the separate closed loop to the anaerobic digestion system of the at least one prime mover fuel source.

30. The waste heat recovery method of claim 25 wherein the working fluid heat removal and condensing subsystem includes a water heating component.

31. The waste heat recovery method of claim 25 wherein the working fluid expander comprises a screw expander.

32. The waste heat recovery method of claim 25 wherein the working expander comprises a twin screw expander.

33. The waste heat recovery method of claim 25 wherein (i) the energy from the expander comprises rotational energy, and (ii) the heated working fluid during at least a portion of generating step (C) comprises working fluid liquid and working fluid vapor.

34. The waste heat recovery method of claim 24 wherein the power receiving component comprises an electric generator.

35. The waste heat recovery method of claim 24 wherein the power receiving component includes one or more among the prime mover, a pump, a combustion engine, a fan, a turbine, or a compressor.

36. The waste heat recovery method of claim 24 wherein the directing step (I) includes directing the thermal energy from said separate secondary heat transfer media in the separate closed loop to a prime mover biogas fuel source.

37. The waste heat recovery method of claim 24 wherein the directing step (I) includes directing the thermal energy from said separate secondary heat transfer media in the separate closed loop to the anaerobic digestion system of the at least one prime mover fuel source.

38. The waste heat recovery method of claim 24 wherein the working fluid heat removal and condensing subsystem includes a water heating component.

39. The waste heat recovery method of claim 24 wherein the working fluid expander comprises a screw expander.

40. The waste heat recovery method of claim 24 wherein the working fluid expander comprises a twin screw expander.

41. The waste heat recovery method of claim 24 wherein (i) the energy from the expander comprises rotational energy, and (ii) the heated working fluid during at least a portion of generating step (C) comprises working fluid liquid and working fluid vapor.

42. A method of power generation using a closed-loop energy transfer system, the method comprising:
    A. with a prime mover, generating prime mover power and prime mover waste heat energy using stored energy contained in prime mover fuel;
    B. with an ORC system, converting the prime mover waste heat energy into ORC power and ORC waste heat energy;
    C. with a prime mover fuel generation system including an anaerobic digestion system, using the ORC waste heat energy to generate prime mover fuel containing stored energy; and
    D. supplying said prime mover fuel containing stored energy to the prime mover for consumption by the prime mover to generate further prime mover power and prime mover waste heat energy by utilizing the stored energy of the prime mover fuel.

43. The method of claim 42 also including as a first step co-locating the prime mover, the ORC system, and the prime mover fuel generation system.

44. The method of claim 42 wherein the prime mover fuel generation system includes a biogas generation system.

45. The method of claim 44 also including the step of generating prime mover fuel that includes, in a working fluid heat removal and condensing subsystem, simultaneously consuming heat from the ORC working fluid and cooling working fluid in the ORC while adding said heat consumed from the ORC working fluid to the lower temperature prime mover fuel generation system for the purpose of producing prime mover fuel.

46. The method of claim 45 wherein the consuming heat step accomplishes the cooling working fluid step.

47. The method of claim 42 wherein the ORC system comprises a screw expander.

48. A power production apparatus comprising:
    A. a prime mover having a first power generation system;
    B. a closed loop organic Rankine cycle system in heat transfer receiving communication with the prime mover; and
    C. a heat consuming prime mover fuel production system including an anaerobic digestion system in heat transfer receiving communication with the closed loop organic Rankine cycle system and in prime mover fuel sending communication with the prime mover configured such that i) the temperature of the heat consuming prime mover fuel production system is lower than the temperature of the closed loop organic Rankine cycle system to allow heat to be transferred from the closed loop organic Rankine cycle system to the heat consuming prime mover fuel production system, and ii) the fuel produced by the heat consuming prime mover fuel production system is communicated to the prime mover for consumption therein so as to generate power via the first power generation system and to produce heat that is communicated to the closed loop organic Rankine cycle system.

49. The power production apparatus of claim 48 wherein the heat consuming prime mover fuel production system includes a biogas production system.

50. The power production apparatus of claim 49 wherein the closed loop organic Rankine cycle system includes a second power generation system.

51. The power production apparatus of claim 49 wherein the heat consuming prime mover fuel production system is in heat transfer receiving communication with a working fluid heat removing cooling and condensing system in the closed loop organic Rankine cycle system.

52. The power production apparatus of claim 48 wherein the closed loop organic Rankine cycle system includes a second power generation system.

53. The power production apparatus of claim 48 wherein the heat consuming prime mover fuel production system is in heat transfer receiving communication with a working fluid heat removing cooling and condensing system in the closed loop organic Rankine cycle system.

54. The power production apparatus of claim 48 wherein the closed loop organic Rankine cycle system comprises a screw expander.

55. The power production apparatus of claim 48 wherein the closed loop organic Rankine cycle system comprises a twin screw expander.

\* \* \* \* \*